(12) United States Patent
Hosoi et al.

(10) Patent No.: US 9,671,346 B2
(45) Date of Patent: *Jun. 6, 2017

(54) PARTICLE DETECTING AND DISCRIMINATING DEVICE AND METHOD

(71) Applicant: Azbil Corporation, Tokyo (JP)

(72) Inventors: Tomoki Hosoi, Tokyo (JP); Daisuke Obara, Tokyo (JP); Masashi Furuya, Tokyo (JP); Seiichirou Kinugasa, Tokyo (JP)

(73) Assignee: AZBIL CORPORATION, Tokyo (JP)

( * ) Notice: Subject to any disclaimer, the term of this patent is extended or adjusted under 35 U.S.C. 154(b) by 82 days.

This patent is subject to a terminal disclaimer.

(21) Appl. No.: 14/749,865

(22) Filed: Jun. 25, 2015

(65) Prior Publication Data

US 2015/0377785 A1 Dec. 31, 2015

(30) Foreign Application Priority Data

Jun. 26, 2014 (JP) .................................. 2014-131841

(51) Int. Cl.
*G01N 21/64* (2006.01)
*G01N 15/14* (2006.01)
*C12Q 1/06* (2006.01)

(52) U.S. Cl.
CPC .......... *G01N 21/6486* (2013.01); *C12Q 1/06* (2013.01); *G01N 15/14* (2013.01);
(Continued)

(58) Field of Classification Search
CPC ....... G01N 21/6486; G01N 2015/1486; G01N 2021/6419; G01J 1/42
(Continued)

(56) References Cited

U.S. PATENT DOCUMENTS 6,198,110 B1 * 3/2001 Kaye .................. G01N 15/1436
250/573
7,295,319 B2 11/2007 Kajii
(Continued)

FOREIGN PATENT DOCUMENTS

JP H08-29331 A 2/1996
JP 2003-139707 A 5/2003
(Continued)

OTHER PUBLICATIONS

Bartek, Rajwa, et al: "Automated classification of bacterial particles in flow by multiangle scatter measurement and support vector machine classifier", Cytometry. Part A, John Wiley, Hoboken, NJ, US, vol. 73A, No. 4, Apr. 1, 2008 (Apr. 1, 2008), pp. 369-379, [retrieved on Dec. 28, 2007].
(Continued)

*Primary Examiner* — Que T Le
(74) *Attorney, Agent, or Firm* — Troutman Sanders LLP

(57) ABSTRACT

A particle detecting device includes: a storing device that stores first boundary information wherein the third light intensity is recorded in a first range at a discriminating boundary for particles of first and second classifications, second boundary information wherein the third light intensity is recorded in a second range at a discriminating boundary for particles of first and second classifications, and discriminating information wherein identifiers for particles of the first and second classifications are recorded in cells bounded and not bounded by the discriminating boundary, respectively; and a particle identifying portion that evaluates a particle being measured as a particle of the first classification when the identifier for a particle of the first classification is acquired based on the measured values for the first and second light intensities and the measured value for the
(Continued)

third light intensity falls between the first and second boundary values.

20 Claims, 12 Drawing Sheets

(52) U.S. Cl.
CPC . *G01N 15/1434* (2013.01); *G01N 2015/1402* (2013.01); *G01N 2015/144* (2013.01); *G01N 2015/1477* (2013.01); *G01N 2015/1488* (2013.01)

(58) Field of Classification Search
USPC ....... 250/222.2, 221, 573–576; 356/335–343
See application file for complete search history.

(56) References Cited

U.S. PATENT DOCUMENTS

| | | |
|---|---|---|
| 2004/0262501 A1 | 12/2004 | Kajii |
| 2013/0077087 A1 | 3/2013 | Janka et al. |

FOREIGN PATENT DOCUMENTS

| | | |
|---|---|---|
| JP | 2011-083214 A | 4/2011 |
| JP | 2012-086105 A | 5/2012 |
| WO | 2009/108223 A2 | 9/2009 |

OTHER PUBLICATIONS

Extended European Search Report dated Oct. 15, 2015, issued in corresponding European Application No. 15173744.2.

Hasegawa, N. et al., Instantaneous Bioaerosol Detection Technology and Its Application, azbil Technical Review, 2-7, Yamatake Corporation, Dec. 2009.

Thornton, Joel A. et al., "Atmospheric NO2: In Situ Laser-Induced Fluorescence Detection at Parts per Trillion Mixing Ratios," Analytical Chemistry, vol. 72, No. 3, Feb. 2000, pp. 528-539.

Nizkorodov, S. A. et al., "Time-resolved fluorescence of NO2 in a magnetic field," vol. 215, No. 6, Chemical Physics Letters, Dec. 17, 1993, pp. 662-667.

* cited by examiner

PARTICLE DETECTING AND DISCRIMINATING DEVICE AND METHOD

CROSS REFERENCE TO RELATED APPLICATION

This application claims priority under 35 U.S.C. §119 to Japanese Patent Application No. 2014-131841, filed on Jun. 26, 2014, the entire content of which being hereby incorporated herein by reference.

FIELD OF TECHNOLOGY

The present disclosure relates to an inspecting technology, and relates to a particle detecting device and particle detecting method.

BACKGROUND

In clean rooms, such as bio clean rooms, airborne microorganism particles and non-microorganism particles are detected and recorded using particle detecting devices. See, for example, Japanese Unexamined Patent Application Publication No. 2011-83214 and N. Hasegawa, et al., *Instantaneous Bioaerosol Detection Technology and Its Application*, azbil Technical Review, 2-7, Yamatake Corporation, December 2009. The state of wear of the air-conditioning equipment of the clean room can be ascertained from the result of the particle detection. Moreover, a record of particle detection within the clean room may be added as reference documentation to the products manufactured within the clean room. Optical particle detecting devices draw in air from a clean room, for example, and illuminate the drawn-in air with light. If a microorganism particle or non-microorganism particle is included in the air, then the particle that is illuminated by the light will produce fluorescence or scattered light will be produced by the particle. Because of this, it is possible to detect the numbers and sizes of microorganism particles and non-microorganism particles that are included in a gas, through detecting the fluorescent and scattered light. Moreover, a technology able to detect accurately particles in not just clean rooms, but in fluids as well, is desired. See, for example, Japanese Unexamined Patent Application Publication Npo. H8-29331.

The intensity of fluorescence emitted from particles may differ depending on the type of particle. Moreover, the intensity of scattered light produced by a particle may also differ depending on the type of particle. Because of this, a method has been proposed for identifying whether a particle is a biologic particle or a non-biologic particle based on the intensity of fluorescence and on the intensity of scattered light. See, for example, US Patent Application Publication No. 2013/0077087.

In order to increase the accuracy of the identification of a particle as a biologic particle or a non-biologic particle, it is necessary to increase the accuracy the discrimination standard. However, high-accuracy discrimination standards can increase the required memory capacity, and decrease the processing speed, in a computer system. Given this, an aspect of the present invention is to provide a particle detecting device, and particle detecting method, that is able to discriminate between biologic particles and non-biologic particles, and that adds little burden to the computer system.

SUMMARY

An aspect of the present invention is a particle detecting device including: a light measuring instrument that measures measured values for intensities of first, second, and third lights of mutually differing wavelengths, produced by particles to be measured; a first boundary information storing portion that stores first boundary information wherein intensities of a third light at a discriminating boundary for a particle of a first classification and a particle of a second classification is recorded in a first range in a two-dimensional table of first and second light intensities; a second boundary information storing portion that stores second boundary information wherein intensity of a third light at the discriminating boundary is recorded in a second range in the two-dimensional table; a discriminating information storing portion that stores discriminating information wherein an identifier for a particle of the first classification is recorded in a cell that is bounded by the discriminating boundaries of the two-dimensional table and an identifier for a particle of the second classification is recorded in a cell that is not bounded by the discriminating boundaries; an information acquiring portion that acquires identifiers for particles of the first and second classifications, from the identifying information, and acquires, from the first and second boundary information, first and second boundary values for the intensity of the third light at the discriminating boundary, based on measured values for the intensities of the first and second lights; and a particle evaluating portion that evaluates that the particle being measured is a particle of the first classification when the identifier for the particle of the first classification is acquired and the measured value for the intensity of the third light is between the first and second boundary values, and evaluates that the particle being measured is a particle of the second classification when the identifier for a particle of the first classification is acquired and the measured value for the intensity of the third light is not between the first and second boundary values or when an identifier for a particle of the second classification is acquired.

In the particle detecting device set forth above: the first and second lights may be lights in the fluorescent band, and the third light may be scattered light. Conversely, the first through third lights may be lights in the fluorescent band. Moreover, the particle of the first classification may be a biologic particle, and the particle of the second classification may be a non-biologic particle. Conversely, the particle of the first classification may be a non-biologic particle, and the particle of the second classification may be a biologic particle.

In the particle detecting device set forth above: the first and second boundary information may be images wherein the intensities of the third light are represented as gradations. Moreover, the first and second boundary information may be grayscale images. Furthermore, the measured value for the intensity of the third light may be converted into a gradation value in the gradation scale. In addition, the image of the first boundary information may correspond to an image wherein a three-dimensional coordinate system of the intensities of the first through third lights, including a multivariate function representing the discriminating boundaries, is observed from above the coordinate indicating the intensity of the third light; and the image of the second boundary information may correspond to an image wherein a three-dimensional coordinate system, including a multivariate function, is observed from below the coordinate indicating the intensity of the third light.

In the particle detecting device set forth above: the discriminating information may correspond to an image that is a slice, at an arbitrary value for the coordinate that indicates the intensity of the third light, in a three-dimensional coordinate system for the intensities of the first through third lights that includes the multivariate function that indicates the discriminating boundaries. Conversely, the discriminating information may correspond to an image that is a slice, at a maximum value, a minimum value, and an intermediate value for the intensity of the third light in the multivariate function, in a three-dimensional coordinate system for the intensities of the first through third lights that includes the multivariate function that indicates the discriminating boundaries. Moreover, the identifying information may be a binary value image.

The particle detecting device set forth above may further include: a degradation information recording portion that records degradation information for the light measuring instruments; and a correcting portion that corrects a measured value for the intensity of the first light, the intensity of the second light, and/or the intensity of the third light. Conversely, the particle detecting device set forth above may further include: a degradation information recording portion that records degradation information for the light measuring instruments; and a correcting portion that corrects the first boundary information and the second boundary information based on the degradation information.

Moreover an aspect of the present invention is a particle detecting method including the steps of: measuring measured values for intensities of first, second, and third lights of mutually differing wavelengths, produced by particles to be measured; storing first boundary information wherein intensities of a third light at a discriminating boundary for a particle of a first classification and a particle of a second classification is recorded in a first range in a two-dimensional table of first and second light intensities; storing second boundary information wherein intensity of a third light at the discriminating boundary is recorded in a second range in the two-dimensional table; storing discriminating information wherein an identifier for a particle of the first classification is recorded in a cell that is bounded by the discriminating boundaries of the two-dimensional table and an identifier for a particle of the second classification is recorded in a cell that is not bounded by the discriminating boundaries; acquiring identifiers for particles of the first and second classifications, from the identifying information, and acquiring first and second boundary values, from the first and second boundary information for the intensity of the third light at the discriminating boundary, based on measured values for the intensities of the first and second lights; and evaluating that the particle being measured is a particle of the first classification when the identifier for the particle of the first classification is acquired and the measured value for the intensity of the third light is between the first and second boundary values, and evaluating that the particle being measured is a particle of the second classification when the identifier for a particle of the first classification is acquired and the measured value for the intensity of the third light is not between the first and second boundary values or when an identifier for a particle of the second classification is acquired.

In the particle detecting method set forth above: the first and second lights may be lights in the fluorescent band, and the third light may be scattered light. Conversely, the first through third lights may be lights in the fluorescent band. Moreover, the particle of the first classification may be a biologic particle, and the particle of the second classification may be a non-biologic particle. Conversely, the particle of the first classification may be a non-biologic particle, and the particle of the second classification may be a biologic particle.

In the particle detecting method set forth above: the first and second boundary information may be images wherein the intensities of the third light are represented as gradations. Moreover, the first and second boundary information may be grayscale images. Furthermore, the measured value for the intensity of the third light may be converted into a gradation value in the gradation scale. In addition, the image of the first boundary information may correspond to an image wherein a three-dimensional coordinate system of the intensities of the first through third lights, including a multivariate function representing the discriminating boundaries, is observed from above the coordinate indicating the intensity of the third light; and the image of the second boundary information may correspond to an image wherein a three-dimensional coordinate system, including a multivariate function, is observed from below the coordinate indicating the intensity of the third light.

In the particle detecting method set forth above: the discriminating information may correspond to an image that is a slice, at an arbitrary value for the coordinate that indicates the intensity of the third light, in a three-dimensional coordinate system for the intensities of the first through third lights that includes the multivariate function that indicates the discriminating boundaries. Conversely, the discriminating information may correspond to an image that is a slice, at a maximum value, a minimum value, and an intermediate value for the intensity of the third light in the multivariate function, in a three-dimensional coordinate system for the intensities of the first through third lights that includes the multivariate function that indicates the discriminating boundaries. Moreover, the identifying information may be a binary value image.

The particle detecting method set forth above may further include: measuring measured values for intensities of first, second, and third lights of mutually differing wavelengths, produced by particles to be measured; correcting a measured value for the intensity of the first light, the intensity of the second light, and/or the intensity of the third light. Conversely, the particle detecting method as set forth above may further include: measuring measured values for intensities of first, second, and third lights of mutually differing wavelengths, produced by particles to be measured; and correcting the first boundary information and the second boundary information based on the degradation information.

the present invention can provide a particle detecting device, and particle detecting method, that is able to discriminate between biologic particles and non-biologic particles, and that adds little burden to the computer system.

BRIEF DESCRIPTIONS OF THE DRAWINGS

DETAILED DESCRIPTION

Figure 1:
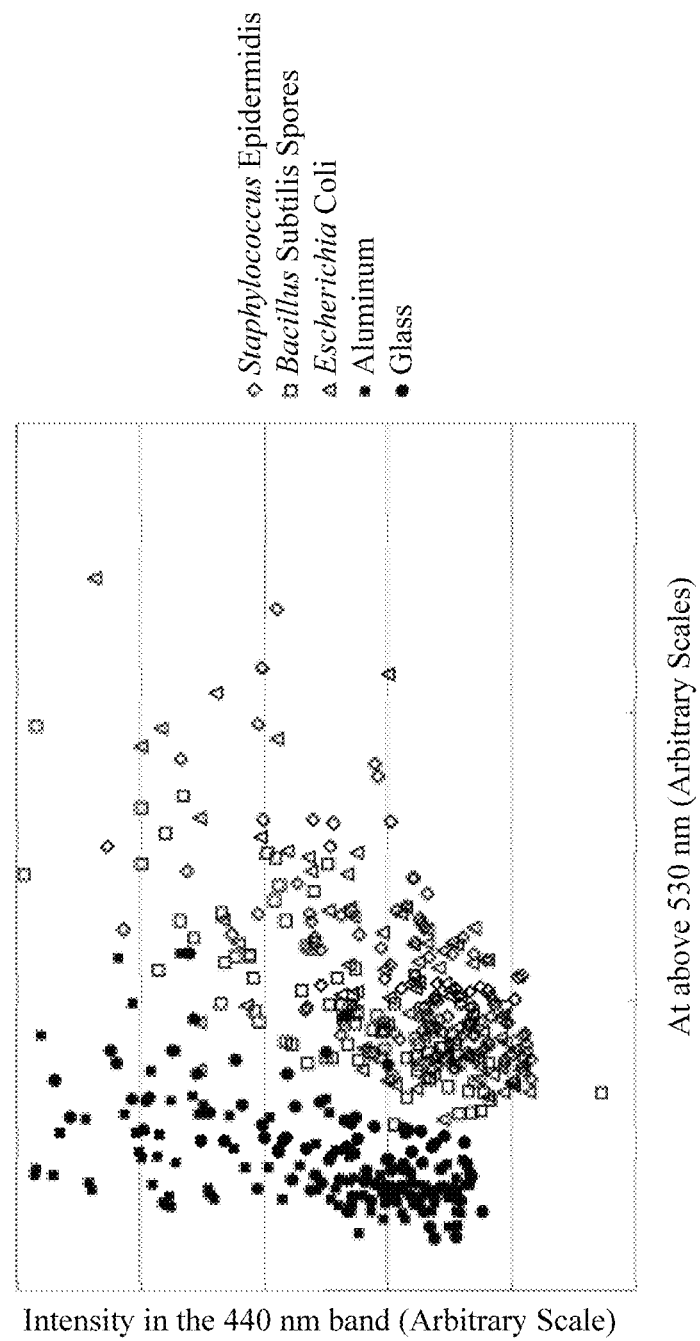
FIG. 1 is a graph showing the relationships of the intensity of light in the 440 nm band, versus the intensity in the band of 530 nm and above, for light emitted from a microorganism and from a substance included in the air in Example according to the present invention.

Examples of the present invention will be described below. In the descriptions of the drawings below, identical or similar components are indicated by identical or similar codes. Note that the diagrams are schematic. Consequently, specific measurements should be evaluated in light of the descriptions below. Furthermore, even within these drawings there may, of course, be portions having differing dimensional relationships and proportions.

Example

When a biologic particle, such as a bacterium, is illuminated with light, scattered light is produced at the biologic particle. Moreover, even when a non-biologic particle, such as of metal or a resin, is illuminated with light, scattered light is produced at the non-biologic particle. The intensity of the scattered light produced by a particle tends to be dependent on the size of the particle. The particle diameters of biologic particles are different depending on the type of microorganism. Moreover, the particle diameters of non-biologic particles are also different depending on the type. Because of this, it is possible to identify the type of measured particle that is included in the fluid from the intensity of the scattered light.

Moreover, when a biologic particle is illuminated with an excitation light, the nicotinamide adenine dinucleotide (NADH) and the riboflavin, and the like, that are included in biologic particle produces fluorescent light. Even when the non-biologic particles are illuminated with light, the non-biologic particle may emit light in the fluorescent band. Fluorescent particles that fall off of a polyester gown, for example, that has been cleaned will emit fluorescence when illuminated with light. Polystyrene particles also emit fluorescence, and then fade.

Moreover, when, for example, a gas includes a nitrogen oxide ($NO_x$), including nitrogen dioxide ($NO_2$), a sulfur oxide ($SO_x$), ozone gas ($O_3$), an aluminum oxide gas, an aluminum alloy, a glass powder, or a decontaminating gas for decontaminating *Escherichia coli* or mold contamination, or the like, substances included in the gas, which may be smaller than particles that produce Mie scattering, will absorb the light to produce light in the fluorescent band.

For example, when nitrogen dioxide absorbs gas, light that is shifted in the red direction is emitted when returning to the base state. The absorption spectrum of nitrogen dioxide has a peak at a wavelength of about 440 nm, but has a broad band between about 100 and 200 nm. Because of this, when, in the presence of nitrogen dioxide, there is an attempt to stimulate NADH fluorescence or flavin fluorescence, which has a wavelength of 405 nm, fluorescence will be stimulated in the nitrogen dioxide as well, which overlaps the absorption spectrum of the excitation beam for the NADH and flavin. Moreover, nitrogen dioxide is generated through a reaction of nitrogen and oxygen in the gas when a substance is combusted. Because of this, even if initially there is no nitrogen dioxide in the gas being inspected, when the gas being inspected is illuminated with a laser beam that has a high beam density, or with a strong electromagnetic emission beam as the excitation beam, substances in the gas may combust to produce nitrogen dioxide, where the nitrogen dioxide may produce fluorescence. Moreover, carbon monoxide and ozone react to form nitrogen dioxide, which may produce fluorescence.

In regards to nitrogen dioxide, please reference Japanese Unexamined Patent Application Publication 2003-139707, Joel A. Thornton, et al., "Atmospheric $NO_2$: In Situ Laser-Induced Fluorescence Detection at Parts per Trillion Mixing Ratios," Analytical Chemistry, Vol. 72, No. 3, February, 2000, pp. 528-539, and S. A. Nizkorodov, et al., "Time-resolved fluorescence of $NO_2$ in a magnetic field," Volume 215, No. 6, Chemical Physics Letters, 17 Dec. 1993, pp. 662-667. In regards to sulfur oxides, reference Japanese Unexamined Patent Application Publication 2012-86105.

After diligent research, the present inventors discovered that when the intensities of light in the fluorescent band, emitted by a substance, are measured at the plurality of wavelengths, the correlation of the intensity of light at one wavelength to the intensity of light that another wavelength will vary depending on the individual substance. For example, FIG. 1 is a graph plotting the intensities of light wavelengths in the band above 530 nm, on the horizontal axis, versus the intensity of light at a wavelength in band near to 440 nm, on the vertical axis, for *Staphylococcus epidermidis, Bacillus subtilis* spores, *Escherichia coli*, glass, and aluminum, illuminated with an excitation beam. As illustrated in FIG. 1, the ratio of the intensities of light at wavelengths in the band of above 530 nm to the intensities of light of the wavelengths in the band near to 440 nm tends to be small for non-biologics and tends to be large for microorganism particles. In this way, the present inventors discovered that measuring the intensities of light in the fluorescent band, emitted by a substance, at each of a plurality of wavelengths and then taking the correlations makes it possible to identify whether a substance is a biologic or a non-biologic.

Figure 2:
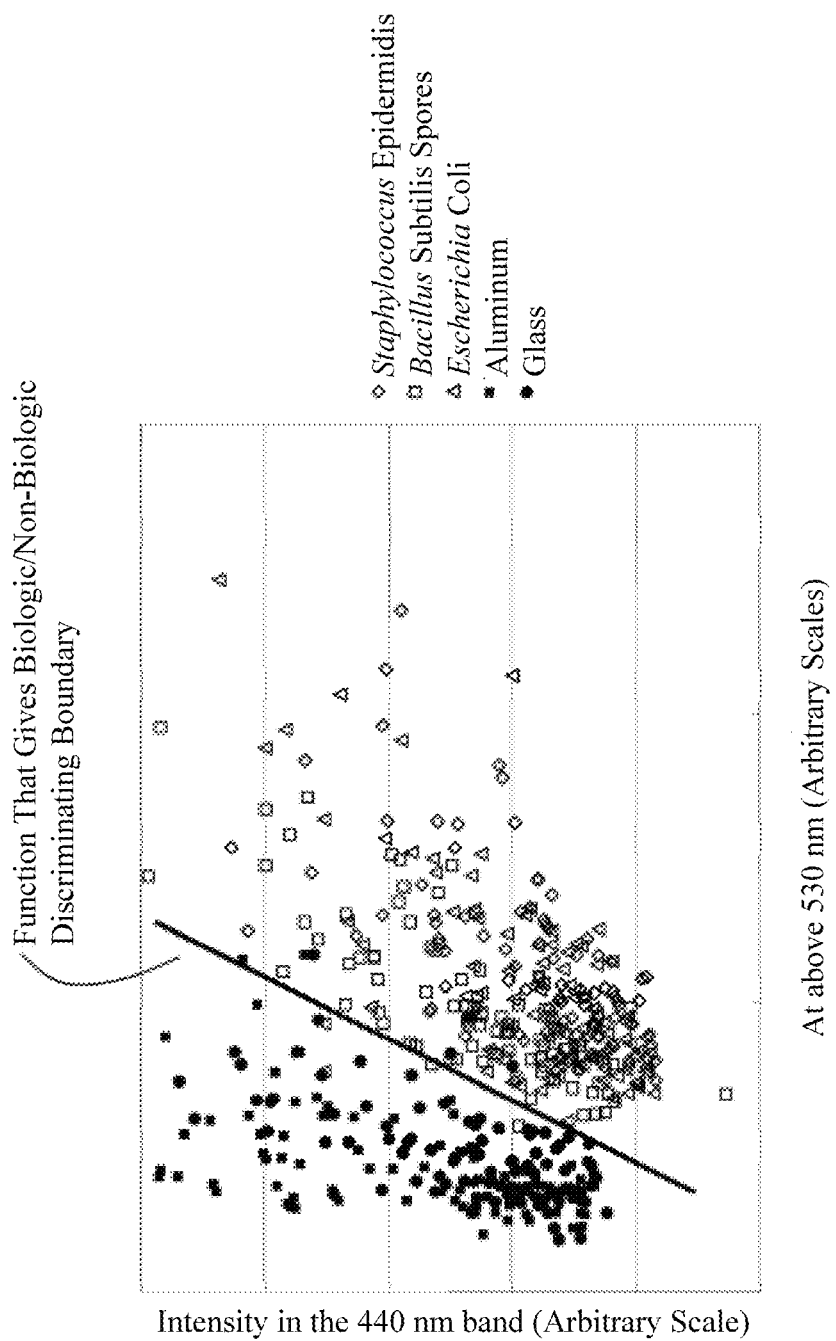
FIG. 2 is a graph showing the relationships of the intensity of light in the 440 nm band, versus the intensity in the band of 530 nm and above, for light emitted from a microorganism and from a substance included in the air in the Example according to the present invention, and the discriminating boundary.

For example, in FIG. 2, when the horizontal axis, which indicates the intensity of light in a first fluorescent band, is defined as the x-axis and the vertical axis, which indicates the intensity of light in a second fluorescent band, is defined as the y-axis, it is possible to define a function $y=f(x)$ that produces a discriminating boundary between biologics and non-biologics. In the example in FIG. 2, particles that yield intensities of light that are plotted in the region of $y>f(x)$ can be classified as non-biologics, and particles that yield intensities of light that are plotted in the region of y<f(x) can be classified as biologics Furthermore, as described above, the intensity of scattered light produced by a particle varies depending on the type of particle. Because of this, it is possible to define a function f(x,y,z) that yields a discriminating boundary between biologics and non-biologics when measured values for intensities of light in a fluorescent band that has a first wavelength, measured values for intensities of light in the fluorescent band having a second wavelength, and the measured values for intensities of scattered light, produced when multiple types of known biologic particles and non-biologic particles are each illuminated with light, are plotted in a three-dimensional coordinate system having the x-axis, the y-axis, and a z-axis that indicates the intensity scattered light.

The function f(x,y,z) that produces the discriminating boundary between biologics and non-biologics can be defined through a non-linear identifier, such as a support vector machine (SVM) that calculates the discriminating boundary, from teaching data, so as to maximize the distances between the individual data points. Note that the identifier is known as a classifier or an identifier. Non-linear identifiers are not limited to support vector machines. For example, an identifier may be used instead that uses boosting in order to increase accuracy through a combination of multiple identifiers, a simulated neural network on a computer with calculation characteristics that look like neural functions, a decision tree, a nearest local search, and empirical inference, or the like, may be used.

Figure 3:
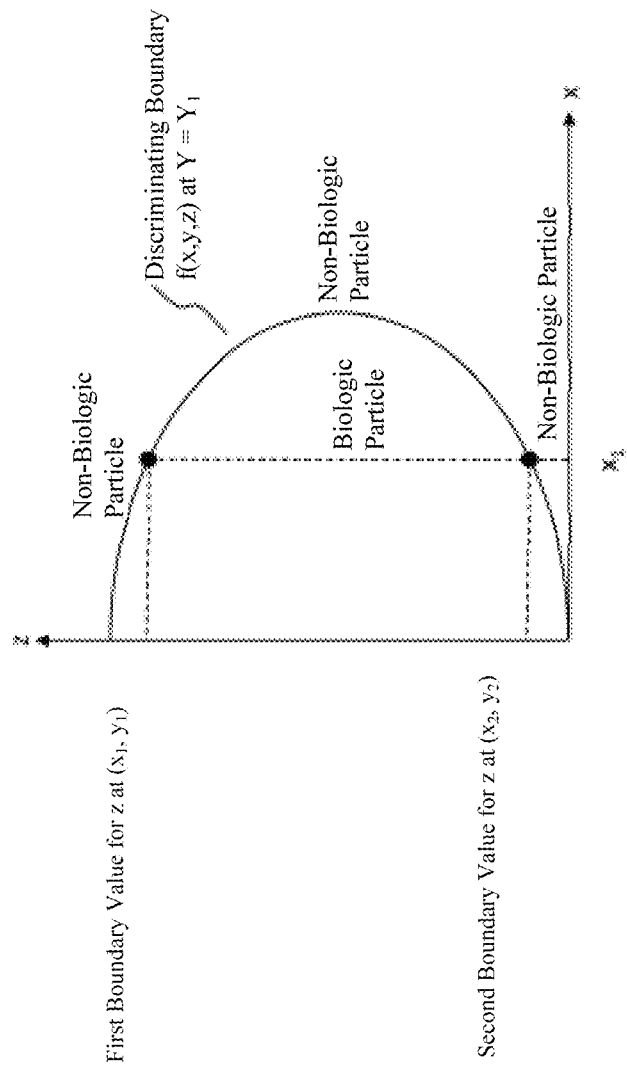
FIG. 3 is a schematic graph of discriminating boundaries in a x-z two-dimensional coordinate system at an arbitrary value for y according to the Example according to the present invention.
Figure 4:
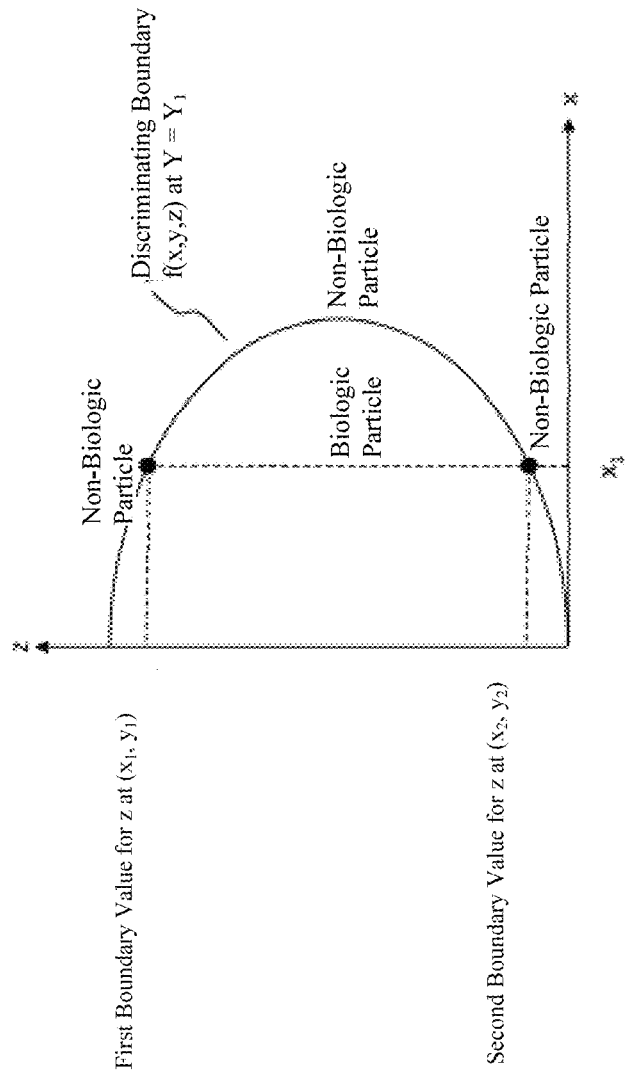
FIG. 4 is a schematic graph of discriminating boundaries in a x-z two-dimensional coordinate system at an arbitrary value for y according to the Example according to the present invention.

For example, when, in the particles that are illuminated with light, there are microorganism particles, non-microorganism particles that are larger than the microorganism particles, and non-microorganism particles that are smaller than the microorganism particles, then, in the three-dimensional coordinate system, as illustrated in FIG. 3, for example, the particles that cause the intensities of light that are plotted in the bounded by the function f(x,y,z) that produces the discriminating boundary scan the classified as biologics, and, for example, as illustrated in FIG. 4, the particles that cause the intensities that are plotted on the outside of the space bounded by the function f(x,y,z) can be classified as non-biologics.

In this case, the function f(x,y,z) that provides the discriminating boundary for biologics and non-biologics, in the three dimensional coordinate system, may be defined in advance, and, thereafter, the intensities of light in the fluorescent band that has the first wavelength, light in the fluorescent band that has the second wavelength, and scattered light, produced when unknown particles are illuminated with the first illumination light, are measured, and if the measured values are plotted in the space that is bounded by the function f(x,y,z), it may be evaluated that the particles that have been measured are biologics, and if the measured values are plotted on the outside of the space bounded by the function f(x,y,z), it can be evaluated that the measured particles are non-biologics.

However, because the data volume of information in a three-dimensional coordinate system is large, it is difficult to build into a computer system, and may be expensive. Moreover, because the volume of data for the information in the three-dimensional coordinate system is large, this may cause a reduction in processing speed in the computer system when evaluating whether an unknown particle is a biologic particle or a non-biologic particle in real time.

Figure 5:
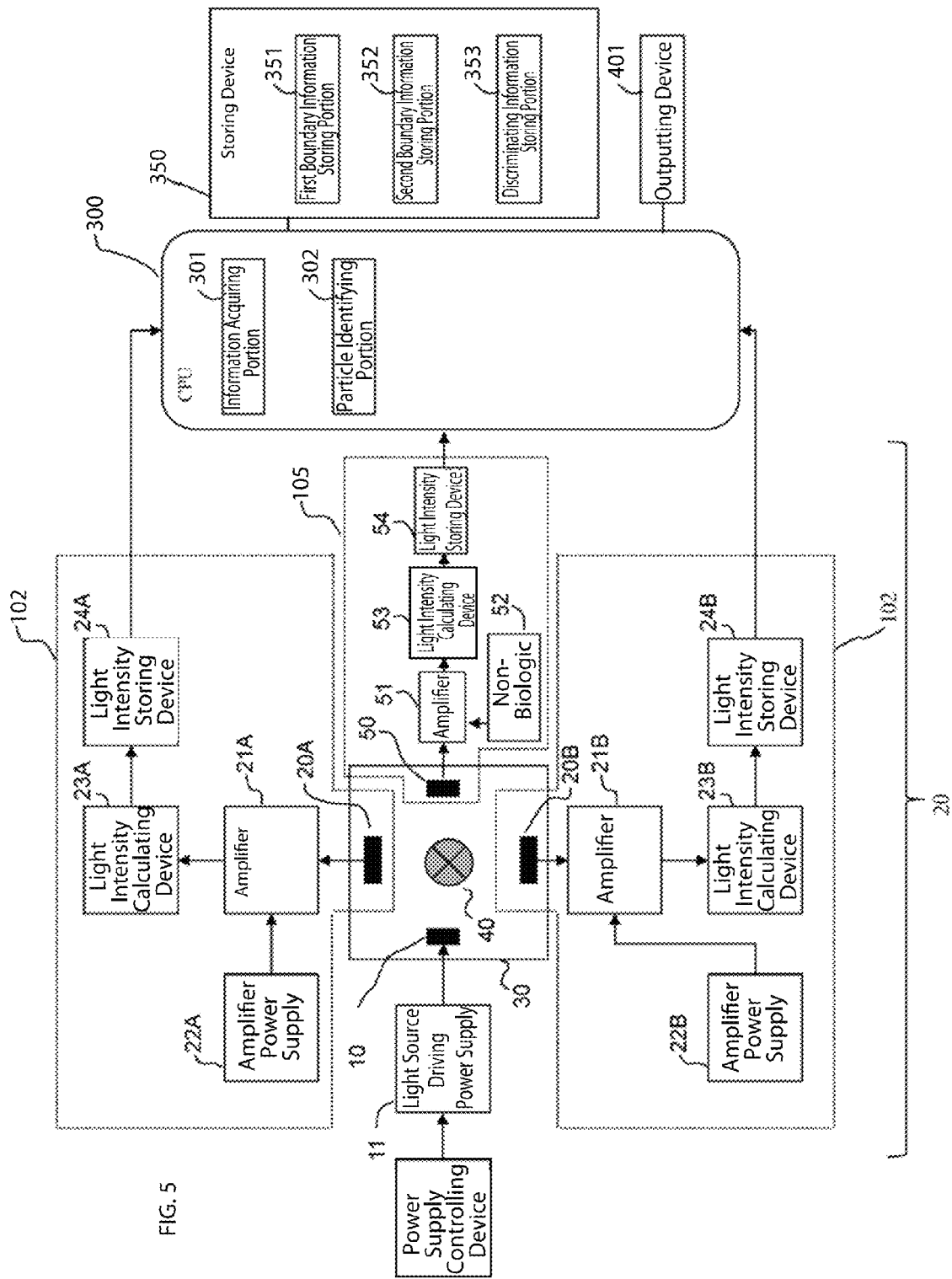
FIG. 5 is a schematic diagram of a detecting device according to the Example according to the present invention.

In contrast, the particle detecting device according to the Example according to the present invention, as illustrated in FIG. 5, is provided with a light measuring instrument 20 for measuring the measured values for the intensity of a first light, having a first wavelength, the intensity of a second light, having a second wavelength, and the intensity of a third light having a third wavelength, produced by the particle that is being measured, and a central calculation processing device (CPU) 300 that is connected electrically to the light measuring instrument 20. The first wavelength, the second wavelength, and the third wavelength are mutually different.

The CPU 300 is connected to a storing device 350. The storing device 350 includes: a first boundary information storing portion 351 for storing, in a two-dimensional table for first and second light intensities, first boundary information wherein intensities of the third light, at a discriminating boundary for particles of a first classification and particles of a second classification, is recorded at a first range of intensities for the third light, acquired in advance; and a second information storing portion 352 for storing, in a two-dimensional table of the intensities of the first and second lights, second boundary information, acquired in advance, wherein intensities of the third light at the discriminating boundary for the particles of the first classification and the particles of the second classification are recorded in a second range of intensities for the third light.

The storing device 350 further includes an identifying information storing portion 353 for storing discriminating information wherein an identifier for a particle of a first classification is recorded in a cell bounded by a discriminating boundary, and an identifier for a particle of the second classification is recorded in a cell bounded by a discriminating boundary, in the two-dimensional table, at one point between the first range and the second range for the intensity of the third light.

The CPU 300 includes: an information acquiring portion 301 for acquiring, from the identifying information, an identifier for the particle of the first classification and an identifier for the particle of the second classification, based on measured values for the first and second light intensities, and for reading out, from the first boundary information, a first boundary value for the intensity of the third light at the discriminating boundary and for reading out, from the second boundary information, a second boundary value for the intensity of the third light at the discriminating boundary; and a particle evaluating portion 302 for evaluating that the particle being measured is a particle of the first classification if the identifier for the particle of the first classification is acquired and the measured value for the intensity of the third line falls between the first boundary value and the second boundary value, and for evaluating that the particle being measured is a particle of the second classification if the identifier for the particle of the first classification is acquired and the measured value for the intensity of the third light does not fall between the first boundary value and the second boundary value or if the identifier for the particle of the second classification is acquired.

An example will be explained below wherein the first and second lights are lights within the fluorescent band and the third light is scattered light. Note that "light of the fluorescent band" includes fluorescence, intrinsic fluorescence, and light that, although not necessarily fluorescence, has a wavelength band that overlaps that of fluorescence. Moreover, an example wherein the particle of the first classification is a biologic particle and the particle of the second classification is a non-biologic particle will be explained below.

A fluid that is to be inspected by a particle detecting device as to whether or not particles are included is sprayed from a nozzle 40. An inspecting light of a broadband wavelength from a light source 10 is directed toward the fluid that is sprayed from the nozzle 40. Note that when a liquid is being inspected, the inspecting light of the broadband wavelength from the light source 10 is directed toward a flow cell, or the like, wherein the liquid is flowing. An example wherein the fluid is a gas will be explained below. A light-emitting diode (LED) or a laser, for example, may be used for the light source 10. The wavelength of the inspecting light may be, for example, between 250 and 550 nm. The inspecting light may be a visible light, or may be ultraviolet radiation. If the inspecting light is visible light, then the wavelength of the inspecting light is, for example, in a range between 400 and 550 nm, for example, 405 nm. If the inspecting light is ultraviolet light, then the wavelength of the inspecting light is, for example, in a range between 300 and 380 nm, for example, 340 nm. However, the wavelengths of the inspecting light are not limited thereto. A light source driving power supply 11 for supplying electric power to the light source 10 is connected to the light source 10. A power supply controlling device 12 for controlling the electric power that is supplied to the light source 10 is connected to the light source driving power supply 11.

The light measuring instrument 20 is provided with: a fluorescent intensity measuring instrument 102 for measuring the intensity of light in a first fluorescent band and intensity of light in a second fluorescent band that are produced by a particle that is included in the fluid sprayed from the nozzle 40 and illuminated by the inspecting light; and a scattered light measuring instrument 105 for measuring scattered light produced by the particle being measured, which is illuminated by the inspecting light. The light source 10, the fluorescent intensity measuring instrument 102, and the scattered light measuring instrument 105 are provided on a frame 30. Moreover, the power supply controlling device 12, the fluorescent intensity measuring instrument 102, and the scattered light measuring instrument 105 are connected electrically to the CPU 300.

The fluorescent intensity measuring instrument 102 detects light in the fluorescent band produced by the particles being measured. The fluorescent intensity measuring instrument 102 includes: a first photodetecting element 20A for detecting light of a fluorescent band at a first wavelength; and a second photodetecting element 20B for detecting light of the fluorescent band at a second wavelength that is different from the first wavelength. Note that the first wavelength may have a band. The same is true regarding the second wavelength. Photodiodes, photoelectron tubes, and the like, may be used for the first photodetecting element 20A and the second photodetecting element 20B, and, when light is detected, the optical energy is converted into electrical energy.

An amplifier 21A, for amplifying the current that is produced by the first photodetecting element 20A, is connected to the first photodetecting element 20A. An amplifier power supply 22A, for supplying electric power to the amplifier 21A, is connected to the amplifier 21A. Moreover, a light intensity calculating device 23A, for calculating the intensity of light detected by the first photodetecting element 20A, by detecting the current that has been amplified by the amplifier 21A, is connected to the amplifier 21A. A light intensity storing device 24A, for storing the intensity of light calculated by the light intensity calculating device 23A, is connected to the light intensity calculating device 23A.

An amplifier 21B, for amplifying the current that is produced by the second photodetecting element 20B, is connected to the second photodetecting element 20B. An amplifier power supply 22B, for supplying electric power to the amplifier 21B, is connected to the amplifier 21B. Moreover, a light intensity calculating device 23B, for calculating the intensity of light detected by the second photodetecting element 20B, by detecting the current that has been amplified by the amplifier 21B, is connected to the amplifier 21B. A light intensity storing device 24B, for storing the intensity of light calculated by the light intensity calculating device 23B, is connected to the light intensity calculating device 23B.

The scattered light measuring instrument 105 detects scattered light produced by a particle being measured, which is illuminated by the inspecting light. The scattered light measuring instrument 105 includes a scattered light photodetecting element 50 for detecting scattered light. A photodiode, or the like, may be used for the scattered light photodetecting element 50, to convert light energy into electrical energy when light is detected.

An amplifier 51 for amplifying the current produced by the scattered light photodetecting element 50 is connected to the scattered light photodetecting element 50. An amplifier power supply 52 for supplying electric power to the amplifier 51 is connected to the amplifier 51. Moreover, a light intensity calculating device 53 for calculating the intensity of the scattered light detected by the scattered light photodetecting element 50 by detecting the current that is amplified by the amplifier 51 is connected to the amplifier 51. A light intensity storing device 54 for storing the intensity of the scattered light that is calculated by the light intensity actuating device 53 is connected to the light intensity calculating device 53.

Figure 6:
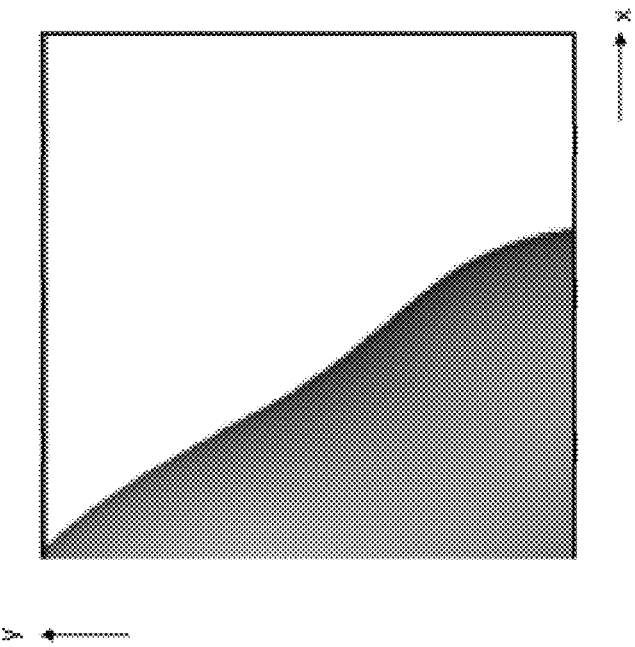
FIG. 6 is a grayscale image of first boundary information in relation to the Example according to the present invention.

For the first boundary information that is stored in the first boundary information storing portion 351, as illustrated in FIG. 6, for example, intensity of scattered light, recorded in a first range scattered light intensity, at the discriminating boundary between the biologic particles and non-biologic particles, acquired in advance, is recorded in each cell of a two-dimensional table that includes a x coordinate for indicating the intensity of light of the first fluorescent band and a y coordinate for indicating the intensity of light in the second fluorescent band. The two-dimensional table includes, for example, 256×256 cells. In this case, the cells in the x direction are given, for example, indices 0 through 255, and the cells in the y direction are also given indices 0 through 255.

The intensity of light is expressed as a voltage signal within a range of, for example, between 0 and 5 V, or the like. The following Equation (1), for example, is used in converting the light intensity into a discrete index I:

$$I=[NI\times(SD/SM)] \qquad (1)$$

Here NI is the number of indices, for example, 256. SD is a measured value for the intensity of the light, expressed as a voltage signal. SM is the maximum value that can be assumed by the light intensity that is expressed as the voltage signal.

The index I, calculated by Equation (1) is an integer number between 0 and 255.

Figure 7:
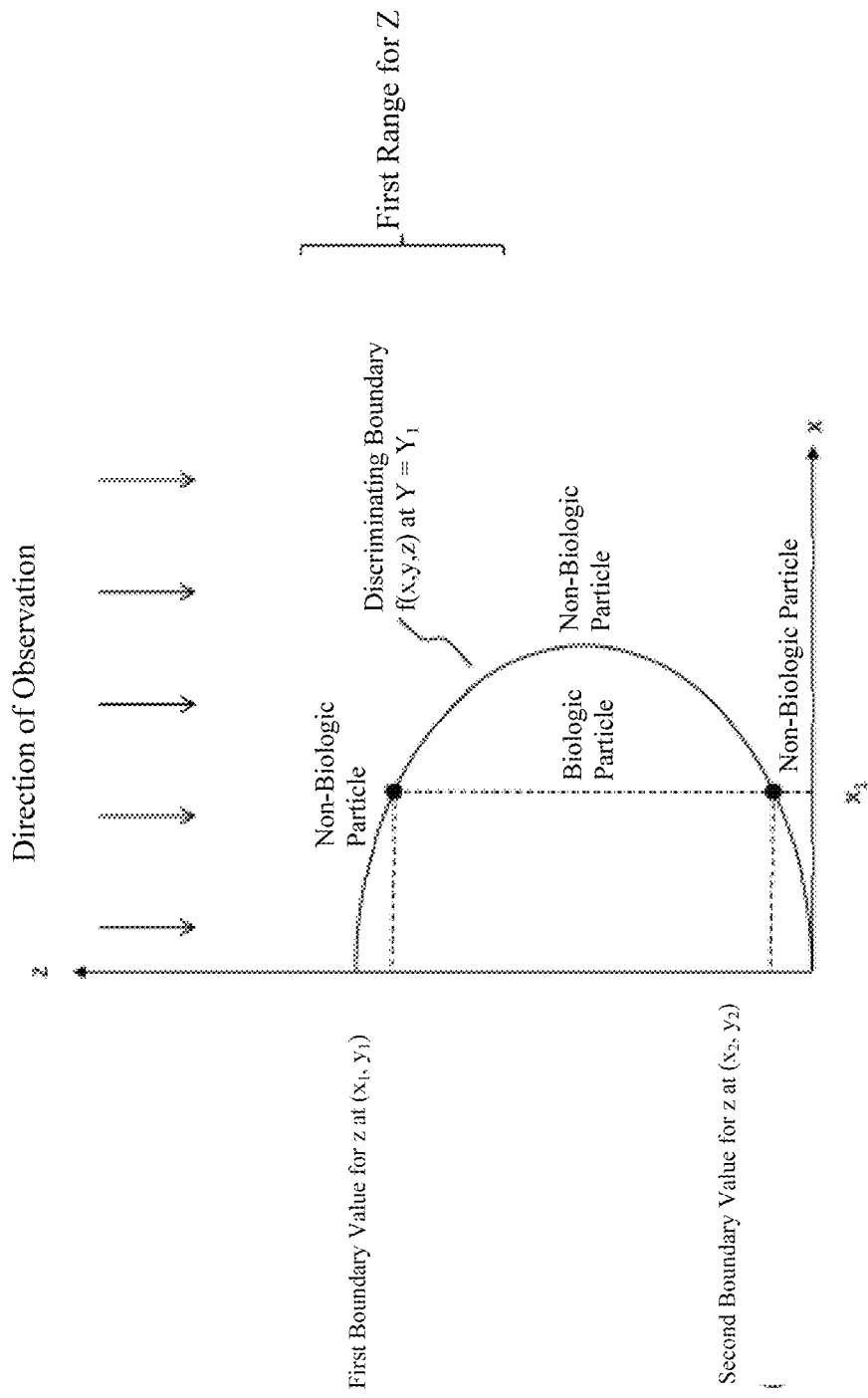
FIG. 7 is a schematic diagram illustrating a method for acquiring first boundary information in relation to the Example according to the present invention.

The first boundary information corresponds to an image wherein a three-dimensional coordinate system, which includes a x coordinate, a y coordinate, and a coordinate that indicates the intensity of scattered light, including a multivariate function f(x,y,z) that provides the discriminating boundary for biologic particles and non-biologic particles, acquired in advance, is viewed from above the z coordinate, as illustrated in FIG. 7. For example, the multivariate function f(x,y,z) that provides the discriminating boundary may be a multivariate function that outputs two values for a dependent variable z relative to a combination of independent variables (x,y). Consequently, the first boundary information describes the distribution of the larger of the two values for the dependent variable z that are outputted from the multivariate function f(x,y,z) in response to the combination of independent variables (x,y). Because of this, the first range for the intensity of the scattered light in the first boundary information is set arbitrarily in accordance with the distribution of the larger of the values for the values of the two dependent variables z that are outputted for the combination of independent variables (x,y).

For example, as illustrated in FIG. 6, the first boundary information is a grayscale image illustrating, in gradations, the intensity of scattered light at the boundary for discriminating between biologic particles and non-biologic particles in each cell of a two-dimensional table. In each individual cell, the intensity of the scattered light at the discriminating boundary for biologic particles and non-biologic particles is, for example, recorded in a 256-gradation gray scale. For example, in the gray scale, high intensities of scattered light are expressed as being bright, and low intensities of scattered light are expressed as being dark. Note that the first boundary information may instead be a color image. For example, Equation (2), below, may be used to convert the intensity of scattered light into a discrete gradation value (pixel value) G:

$$G=[NG \times (SD/SM)] \qquad (2)$$

Here NG is the number of gradations, for example, 256. SD is a measured value for the intensity of the light, expressed as a voltage signal. SM is the maximum value that can be assumed by the light intensity that is expressed as the voltage signal. The gradation value (pixel value) G, calculated by Equation (2) is an integer number between 0 and 255.

The parts wherein the multivariate function f(x,y,z) that indicates the identifying boundary does not exist in the three-dimensional coordinate system are, for example, caused to be the brightest in the image for the first boundary information. Note that the gradations for the coordinates for those parts may instead be the darkest. For example, if the image for the first boundary information is of a 256-gradation scale, then the gradation value (pixel value) for those parts should be 0 or 255.

Figure 8:
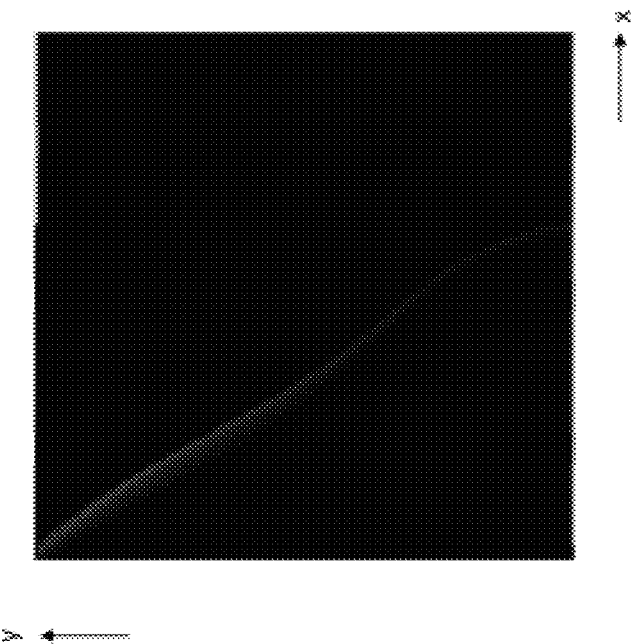
FIG. 8 is a grayscale image of second boundary information in relation to the Example according to the present invention.

For the second boundary information that is stored in the second boundary information storing portion 352, illustrated in FIG. 5, as illustrated in FIG. 8, for example, the intensity distribution of scattered light, recorded in a first range scattered light intensity, at the discriminating boundary between the biologic particles and non-biologic particles, acquired in advance, is recorded in each cell of a two-dimensional table that includes a x coordinate for indicating the intensity of light of the second fluorescent band and a y coordinate for indicating the intensity of light in the second fluorescent band. The two-dimensional table of the second boundary information includes, for example, 256×256 cells. Moreover, the range of the x coordinate and of the y coordinate in the second boundary information is the same as the range of the x coordinate and of the y coordinate in the first boundary information.

Figure 9:
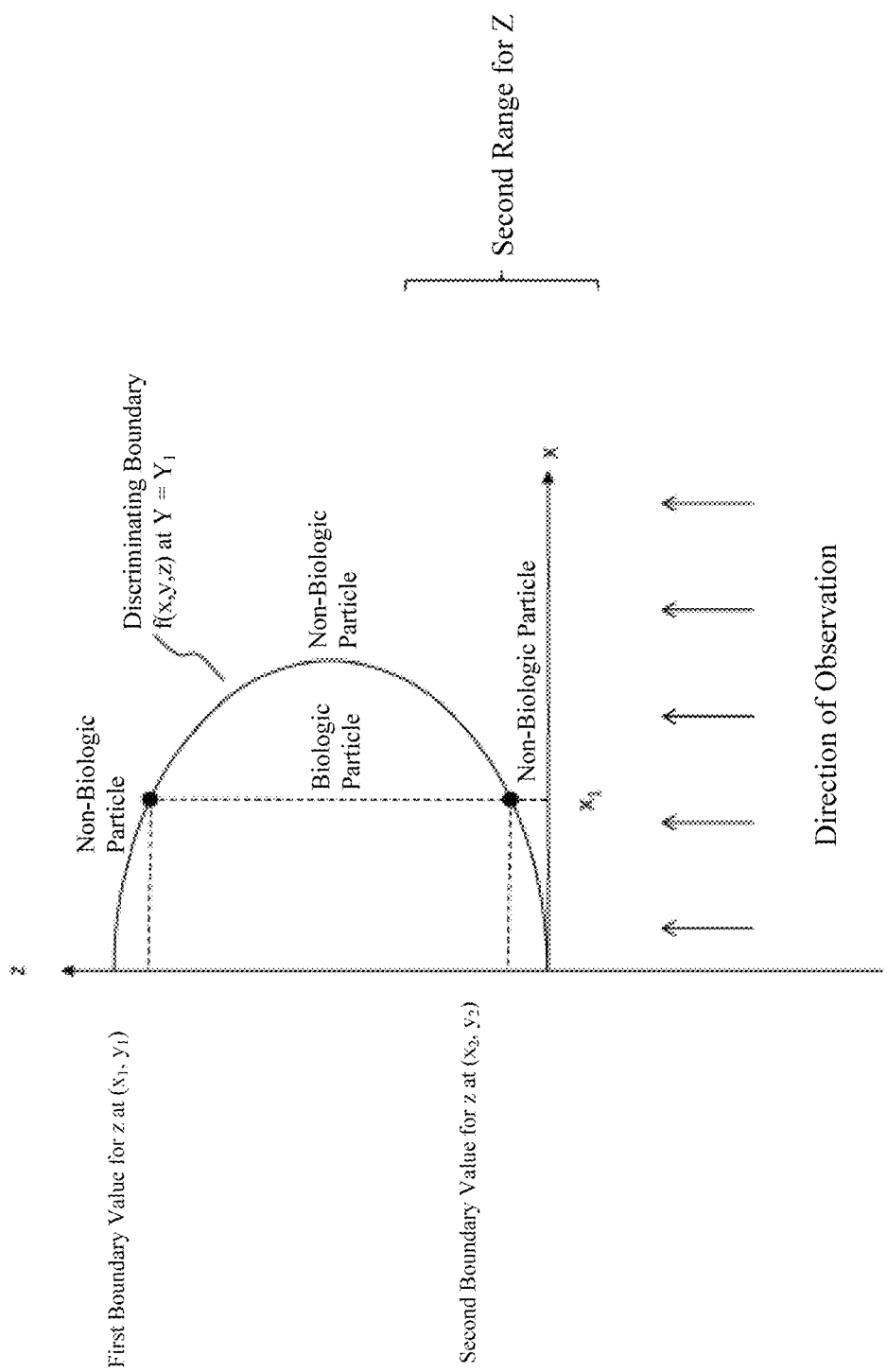
FIG. 9 is a schematic diagram illustrating a method for acquiring second boundary information in relation to the Example according to the present invention.

The second boundary information corresponds to an image wherein a three-dimensional coordinate system, which includes a x coordinate, a y coordinate, and a z coordinate, including a multivariate function f(x,y,z) that provides the discriminating boundary, acquired in advance, is viewed from below the z coordinate, as illustrated in FIG. 9. Consequently, the second boundary information describes the distribution of the smaller of the two values for the dependent variable z that are outputted in response to the combination of independent variables (x,y). Because of this, the second range for the intensity of the scattered light in the second boundary information is set arbitrarily in accordance with the distribution of the smaller of the values for the values of the two dependent variables z that are outputted from the multivariate function f(x,y,z) for the combination of independent variables (x,y). Moreover, the first range and the second range for the intensity of scattered light may partially overlap, however, the first range includes a value that is greater than the second range, and the second range includes a value that is less than the first range.

For example, the second boundary information is a grayscale image illustrating, in gradations, the intensity of scattered light at the boundary for discriminating between biologic particles and non-biologic particles in each cell of a two-dimensional table. In each individual cell, the intensity of the scattered light at the discriminating boundary for biologic particles and non-biologic particles is, for example, recorded in a 256-gradation gray scale. For example, in the gray scale, high intensities of scattered light are expressed as being bright, and low intensities of scattered light are expressed as being dark. Note that the second boundary information may instead be a color image.

The parts wherein the multivariate function f(x,y,z) that indicates the identifying boundary does not exist in the three-dimensional coordinate system are, for example, caused to be the darkest in the image for the second boundary information. Note that the gradations for the coordinates for those parts may instead be the lightest. For example, if the image for the second boundary information is of a 256-gradation scale, then the gradation value (pixel value) for those parts should be 0 or 255.

For example, referencing FIG. 7 and FIG. 9, a particle that has the intensities of light in the first and second fluorescent bands with the values in one combination of (x,y), and having a scattered light intensity that is greater than the first boundary value for the intensity of scattered light in the discriminating boundary recorded in the first boundary information, is a non-biologic particle. Moreover, a particle that has the intensities of light in the first and second fluorescent bands with the values in one combination of (x,y), having a scattered light intensity that is less than the first boundary value for the intensity of scattered light, and having a scattered light intensity that is greater than the second boundary value for the intensity of scattered light in the discriminating boundary recorded in the second boundary information, is a biologic particle. Moreover, a particle that has the intensities of light in the first and second fluorescent bands with the values in one combination of (x,y), and having a scattered light intensity that is less than the second boundary value for the intensity of scattered light in the discriminating boundary recorded in the second boundary information, is a non-biologic particle.

The discriminating information that is stored in the discriminating information storing portion 353 illustrated in FIG. 5 is, for example, a two-dimensional table that is a slice of the multivariate function f(x,y,z) that provides the discriminating boundary between biologics and non-biologics for the value at one arbitrary points between the first range and the second range of the z coordinate in a three-dimensional coordinate system. The arbitrary value of the z coordinate is, for example, an intermediate value between the maximum value and the minimum value for the intensity of the scattered light in the multivariate function f(x,y,z).

The two-dimensional table for the discriminating information includes, for example, 256×256 cells. Moreover, the ranges for the x coordinate and the y coordinate in the discriminating information are the same as the ranges for the x coordinate and the y coordinate in the first and second boundary information. The two-dimensional table for the discriminating information records an identifier for a biologic particle in each cell in the region bounded by the multivariate function f(x,y,z) and records an identifier for a non-biologic particle in each cell of the region not bounded by the multi-variable function f(x,y,z).

Figure 10:
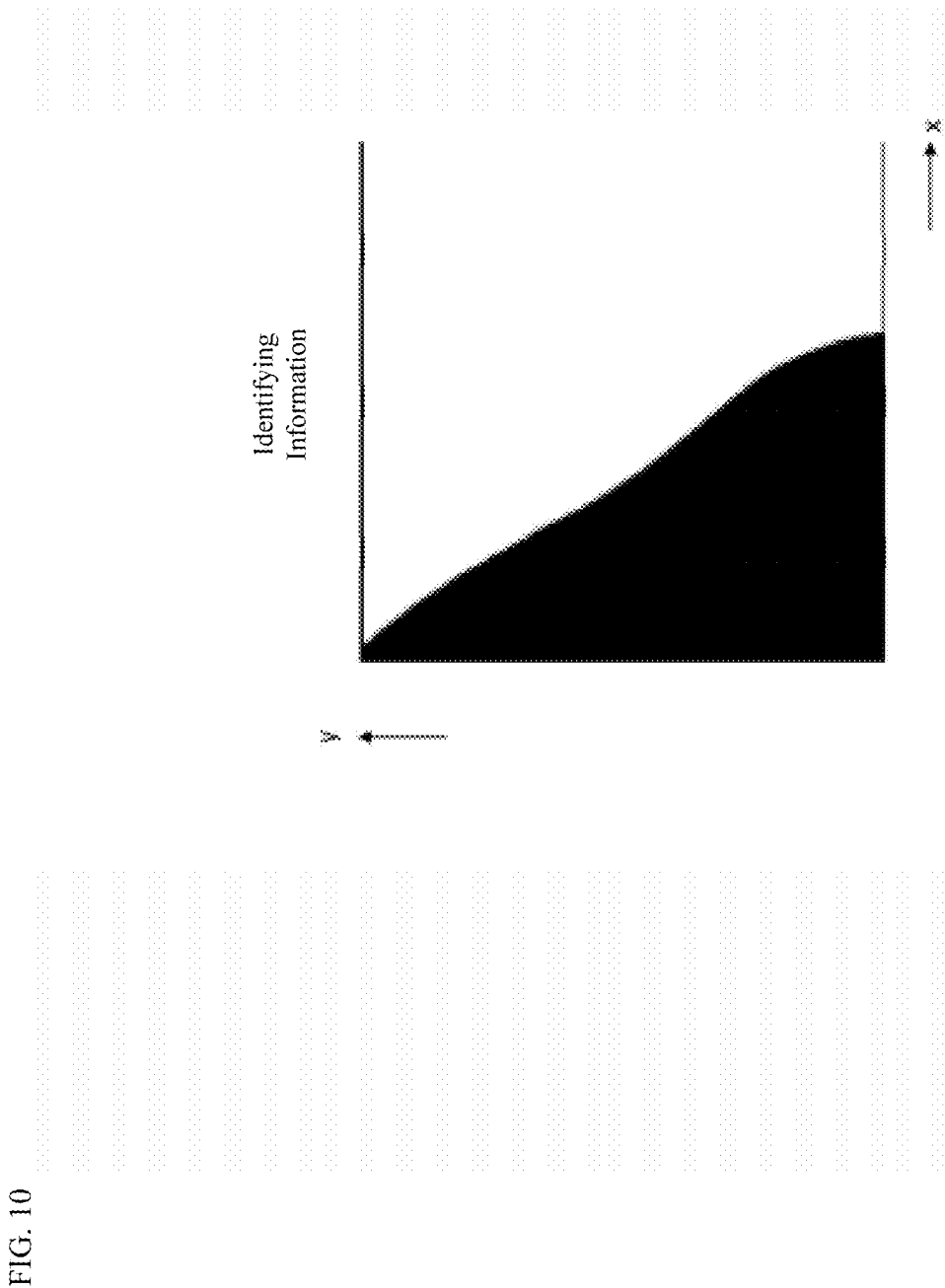
FIG. 10 is a binary value image for identifying information in relation to the Example according to the present invention.

The discriminating information is, for example, a black-and-white binary value image such as shown in FIG. 10, where each cell in the region that is bounded by the multivariate function f(x,y,z) is expressed in black, as the identifier for biologic particles, and each cell in the region that is not bounded by the multivariate function f(x,y,z) is expressed in white as the identifier for non-biologic particles. Note that the colors assigned to the identifier for the biologic particles and to the identifier for the non-biologic particles may be any colors, insofar as they are mutually different.

The information acquiring portion 301 illustrated in FIG. 5 uses, for example, Equation (1), above, to specify a cell at the coordinate (x,y) in the two-dimensional table of the discriminating information, illustrated in FIG. 10, corresponding to the measured value for the intensity of light in the first fluorescent band and the measured value for the intensity of light in the second fluorescent band, produced by the particle being measured. Moreover, the information acquiring portion 301 acquires data on the color of the binary value image at the cell of the specified coordinate (x,y). For example, if the cell for the specified coordinate (x,y) is black, then the information acquiring portion 301 acquires, from the identifying information, black as the identifier for the biologic particle. Moreover, if the cell of the specified coordinate (x,y) is white, then the information acquiring portion 301 acquires, from the identifying information, white as the identifier for the non-biologic particle.

The information acquiring portion 301 illustrated in FIG. 5 specifies a cell at the coordinate (x,y) in the two-dimensional table of the first boundary information, illustrated in FIG. 6, corresponding to the measured value for the intensity of light in the first fluorescent band and the measured value for the intensity of light in the second fluorescent band, produced by the particle being measured. Moreover, the information acquiring portion 301 acquires the first boundary value for the intensity of the scattered light at the discriminating boundary between biologics and non-biologics at the cell of the specified coordinate (x,y).

Furthermore, The information acquiring portion 301 specifies a cell at the coordinate (x,y) in the two-dimensional table of the second boundary information, illustrated in FIG. 8, corresponding to the measured value for the intensity of light in the first fluorescent band and the measured value for the intensity of light in the second fluorescent band, produced by the particle being measured. Moreover, the information acquiring portion 301 acquires the second boundary value for the intensity of the scattered light at the discriminating boundary between biologics and non-biologics at the cell of the specified coordinate (x,y).

The particle evaluating portion 302, illustrated in FIG. 5, evaluates whether or not the measured value for the intensity of scattered light produced by the particle being measured, which produces light in the first and second fluorescent bands, is between the first boundary value and the second boundary value for the intensity of scattered light acquired by the information acquiring portion 301. For example, if the first and second boundary values are expressed as gradient values (pixel values), then the particle evaluating portion 302 uses Equation (2), above to convert the measured value for the intensity of scattered light into a gradation value (a pixel value) in this gradation and then compares to the first and second boundary values.

When an identifier for a biologic particle is acquired and the measured value for the intensity of scattered light is between the first boundary value and the second boundary value, then the particle evaluating portion 302 evaluates that the particle being measured is a biologic particle. Moreover, if despite an identifier for a biologic particle being acquired, the measured value for the intensity of scattered light is not between the first boundary value and the second boundary value, then the particle evaluating versus 302 evaluates that the particle being measured is a non-biologic particle. Furthermore, if an identifier for a non-biologic particle is acquired, then the particle evaluating portion 302 evaluates that the particles being measured is a non-biologic particle.

An outputting device 401 is connected to the CPU 300. The outputting device 401 outputs the evaluation result by the particle evaluating portion 302. A display, a printer, an audio device, or the like, may be used for the outputting device 401.

Figure 11:
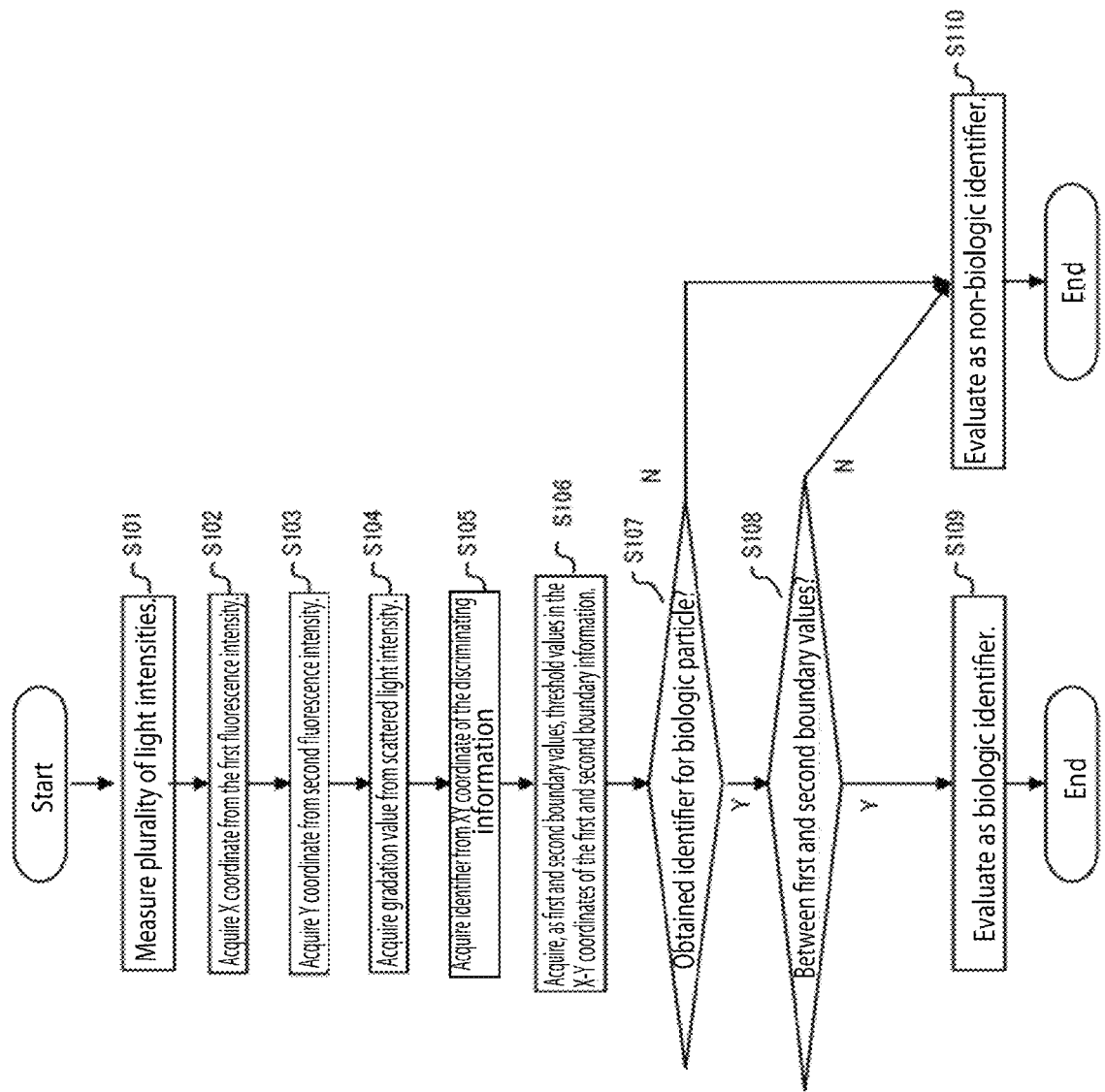
FIG. 11 is a flowchart illustrating the method for detecting particles according to the Example according to the present invention.

A particle detecting method according to the Example will be explained next, referencing the flowchart illustrated in FIG. 11.

In Step S101, a flow of gas is sprayed from the nozzle 40. Moreover, an inspecting light is directed toward the gas flow from the light source 10. When a particle is included in the gas flow, scattered light is produced at the particle that is illuminated by the inspecting light. Moreover, the particle that is illuminated by the inspection light emits light in first and second fluorescent bands. The scattered light is detected by a scattered light photodetecting element 50. The light of the first fluorescent band is detected by the first photodetecting element 20A, and the light of the second fluorescent band is detected by the second photodetecting element 20B.

In Step S102, the information acquiring portion 301 uses Equation (1), above, to convert the measured value for the intensity of light in the first fluorescent band into an index. The index that indicates the measured value for the intensity of light in the first fluorescent band corresponds to the x coordinate in the two-dimensional table. In Step S103, the information acquiring portion 301 uses Equation (2), above, to convert the measured value for the intensity of light in the second fluorescent band into an index. The index that indicates the measured value for the intensity of light in the second fluorescent band corresponds to the y coordinate in the two-dimensional table. In the Step S104, the information acquiring portion 301 uses Equation (2) to convert the measured value for the intensity of scattered light into a gradation value.

In Step S105, the information acquiring portion 301 reads out the discriminating information from the discriminating information storing portion 353. Following this, the information acquiring portion 301 reads out, from the two-dimensional table of the discriminating information, the identifier at the coordinate (x,y) that corresponds to the measured values for the intensities of light in the first and second fluorescent bands.

In Step S106, the information acquiring portion 301 reads out the first boundary information from the first boundary information storing portion 351. Following this, the information acquiring portion 301 reads out, from the two-dimensional table for the first boundary information, the gradation value, as the first boundary value for the intensity of the scattered light, at the coordinate (x,y) that corresponds to the measured values for the intensities of lights in the first and second fluorescent bands. Moreover, the information acquiring portion 301 reads out the second boundary information from the second boundary information storing portion 352. Following this, the information acquiring portion 301 reads out, from the two-dimensional table for the second boundary information, the gradation value, as the second boundary value for the intensity of the scattered light, at the coordinate (x,y) that corresponds to the measured values for the intensities of lights in the first and second fluorescent bands.

In Step S107, the particle evaluating portion 302 evaluates whether the identifier acquired by the information acquiring portion 301 is an identifier for a biologic particle or an identifier for a non-biologic particle. If the evaluation is that it is an identifier for a biologic particle, then processing advances to Step S108. Moreover, if the identifier is for a non-biologic particle, then processing advances to Step S110.

In Step S108, the particle evaluating portion 302 evaluates whether or not the gradation value that indicates the measured value for the intensity of scattered light falls between the gradation value that indicates the first boundary value for the intensity of scattered light and the gradation value that indicates the second boundary value for the intensity of scattered light. If the measured value for the intensity of scattered light falls between the first boundary value for the intensity of scattered light and the second boundary value for the intensity of scattered light, then processing advances to Step S109. If the measured value for the intensity of scattered light does not fall between the first boundary value for the intensity of scattered light and the second boundary value for the intensity of scattered light, then processing advances to Step S110.

If an identifier for a biologic particle is acquired and the measured value for the intensity of scattered light falls between the first boundary value for the intensity of scattered light and the second boundary value for the intensity of scattered light, then, in Step S109, the particle evaluating portion 302 evaluates that the particle is a biologic particle. If an identifier for a biologic particle is acquired by the measured value for the intensity of scattered light does not fall between the first boundary value for the intensity of scattered light and the second boundary value for the intensity of scattered light, then, in Step S110, the particle evaluating portion 302 evaluates that the particle is a non-biologic particle. Moreover, even if an identifier for a non-biologic particle has been acquired, in Step S110 the particle evaluating portion 302 evaluates that the particle is a non-biologic particle. In Step S109 and Step S110, the particle evaluating portion 302 outputs the particle classification evaluation result to the outputting device 401.

There is a tendency for the volume of data in a three-dimensional coordinate system to be large. For example, when 256 index levels are assigned each for the x direction, the y direction, and the z direction, then the three-dimensional coordinate system will be given in a table that is structured from 256×256×256 cells. In contrast, in the particle detecting device according to the Example, the first boundary information and the second boundary information and the discriminating information are each given in two-dimensional coordinate systems, for example, given in tables that are structured from, for example, 256×256 cells. Because of this, it is possible to control the volume of data more than is possible with a three-dimensional coordinate system, through the use of at least three sets of 256×256 cells. However, the number of cells is not limited thereto.

Another Example

Figure 12:
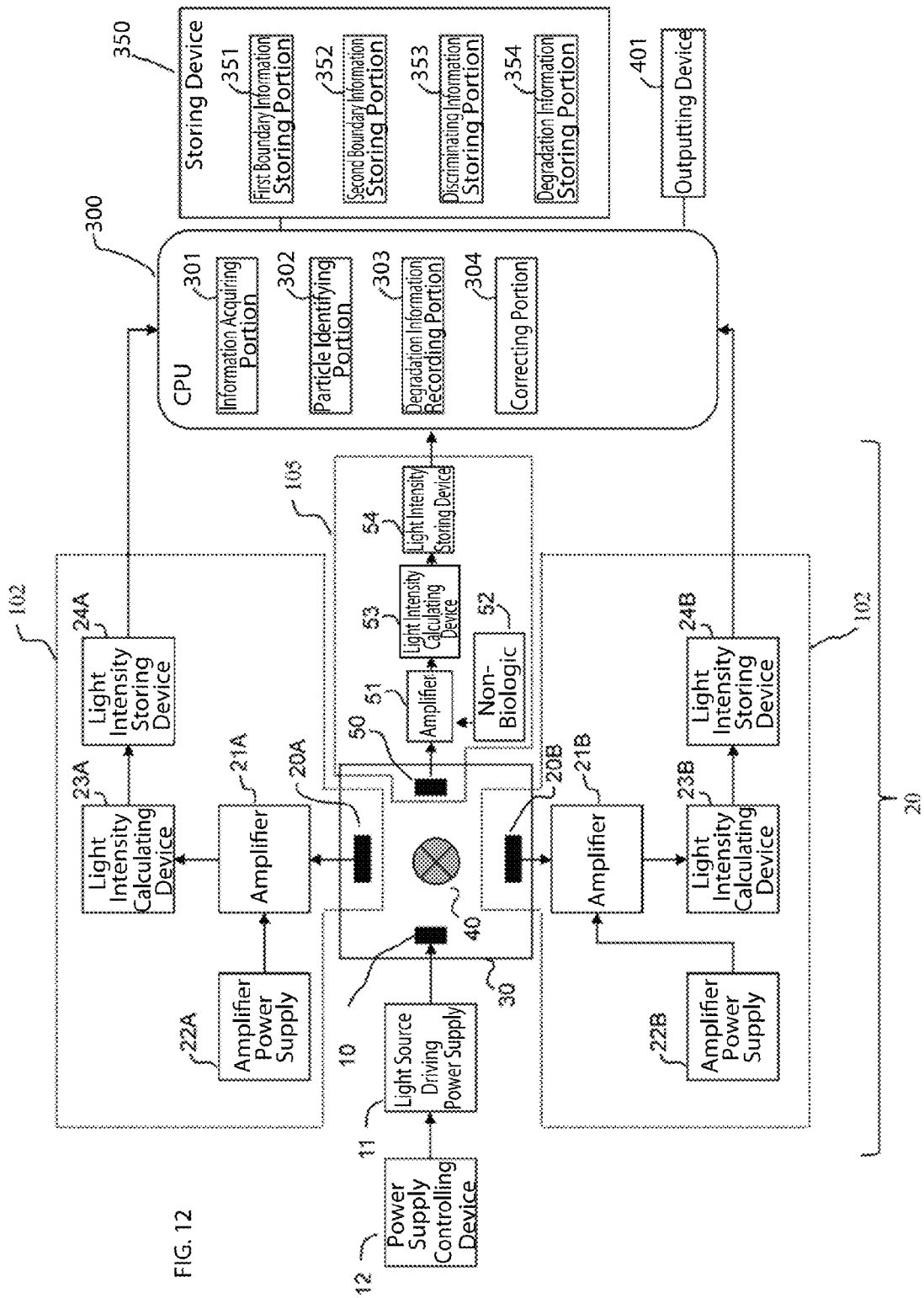
FIG. 12 is a schematic diagram of a detecting device according to Another Example according to the present invention.

A particle detecting device according to Another Example according to the present invention, as illustrated in FIG. 12, further includes: a degradation information recording portion 303 for recording degradation information for the light measuring instrument 20; and a correcting portion 304 for correcting, based on the degradation information, the measured value for the intensity of the first light of the first wavelength, the measured value for the intensity of the second light of the second wavelength, and/or the measured value for the intensity of the third light of the third wavelength.

For example, over time the scattered light photodetecting element 50, the first photodetecting element 20A, and the second photodetecting element 20B of the light measuring instrument 20 may experience degradation so that the detection sensitivity thereof is reduced. The degradation information recording portion 303 records, and stores in the degradation information storing portion 354 of the storing device 350, the elapsed time that has elapsed since the particle detecting device was shipped from the factory, the total time over which the particle detecting device has operated, the total time over which the first photodetecting element 20A and the second photodetecting element 20B have each detected light, and the like, as degradation information.

The correcting portion 304 reads out the degradation information from the degradation information storing portion 354. For example, if the degradation information is a record of the total amount of time over which light has been detected by the scattered light photodetecting element 50, the first photodetecting element 20A, and the second photodetecting element 20B, respectively, then the correcting portion 304 increases the values by multiplying by a coefficient, depending on the respective total time over which light has been detected, the measured value for the intensity of light in the first fluorescent band, the measured value for the intensity of light in the second fluorescent band, and the measured value for the intensity of scattered light.

Conversely, the correcting portion 304 may correct the first boundary information, the second boundary information, and the identifying information based on the degradation information. Specifically, the correcting portion 304 may reduce the x coordinate of the first boundary information, the second boundary information, and the discriminating information by multiplying with a coefficient in accordance with the reduction in photodetecting sensitivity of the first photodetecting element 20A. Conversely, the correcting portion 304 may reduce the y coordinate of the first boundary information, the second boundary information, and the discriminating information by multiplying with a coefficient in accordance with the reduction in photodetecting sensitivity of the second photodetecting element 20B. Moreover, the correcting portion 304 may reduce the gradation value (pixel value) of the first boundary information and the second boundary information through multiplying with a coefficient in accordance with the reduction in the photodetecting sensitivity of the scattered light photodetecting element 50, and so forth.

The particle detecting device according to the Another Example enables extended high precision discrimination of particles even given the occurrence of degradation in the light measuring instrument 20.

Other Example

While there are descriptions of examples as set forth above, the descriptions and drawings that form a portion of the disclosure are not to be understood to limit the present disclosure. A variety of alternate examples and operating technologies should be obvious to those skilled in the art.

For example, while the above explanations are for the examples wherein the first and second lights are lights in the fluorescent band and the third light is scattered light, the wavelengths for the first through third lights are arbitrary, insofar as they are mutually different. For example, the first through third lights may be lights in the fluorescent band.

Moreover, while the above explanations are for the examples wherein the particles of the first classification are biologic particles and the particles of the second classification are non-biologic particles, depending on the form of the multivariate function that indicates the discriminating boundary between the particles of the first classification and the particles of the second classification, the particles of the first classification may be non-biologic particles, and the particles of the second classification may be biologic particles. Furthermore, the particles of the first specification may be a specific type of biologic particles with the particles of the second classification being another type of biologic particles, or, conversely, the particles of the first classification may be a specific type of non-biologic particles with the particles of the second classification being another type of non-biologic particles. The method of classifying the particles is arbitrary.

Moreover, while the two-dimensional tables for the first and second boundary information and for the discriminating information in the present examples are images, values for the scattering light intensities or the identifiers may be recorded as character strings in the respective cells in the two-dimensional tables.

In this way, the present disclosure should be understood to include a variety of examples, and the like, not set forth herein.

The invention claimed is:

1. A particle detecting device comprising:
a light measuring instrument that measures measured values for intensities of first, second, and third lights of mutually differing wavelengths, produced by particles to be measured;
a first boundary information storing portion that stores first boundary information wherein intensities of a third light at a discriminating boundary for a particle of a first classification and a particle of a second classification is recorded in a first range in a two-dimensional table of first and second light intensities;
a second boundary information storing portion that stores second boundary information wherein intensity of a third light at the discriminating boundary is recorded in a second range in the two-dimensional table;
a discriminating information storing portion that stores discriminating information wherein an identifier for a particle of the first classification is recorded in a cell that is bounded by the discriminating boundaries of the two-dimensional table and an identifier for a particle of the second classification is recorded in a cell that is not bounded by the discriminating boundaries;
an information acquiring portion that acquires identifiers for particles of the first and second classifications, from the discriminating information, and acquires first and second boundary values, from the first and second boundary information, for the intensity of the third light at the discriminating boundary, based on measured values for the intensities of the first and second lights; and
a particle evaluating portion that evaluates that the particle being measured is a particle of the first classification when the identifier for the particle of the first classification is acquired and the measured value for the intensity of the third light is between the first and second boundary values, and evaluates that the particle being measured is a particle of the second classification either when the identifier for a particle of the first classification is acquired and the measured value for the intensity of the third light is not between the first and second boundary values or when an identifier for a particle of the second classification is acquired.

2. The particle detecting device as set forth in claim 1, wherein:
the first and second lights are lights in the fluorescent band, and the third light is scattered light.

3. The particle detecting device as set forth in claim 1, wherein:
the particle of the first classification is a biologic particle; and
the particle of the second classification is a non-biologic particle.

4. The particle detecting device as set forth in claim 1, wherein:
the particle of the first classification is a non-biologic particle; and
the particle of the second classification is a biologic particle.

5. The particle detecting device as set forth in claim 1, wherein:
the first and second boundary information are images wherein the intensities of the third light are represented as gradations.

6. The particle detecting device as set forth in claim 5, wherein:
the first and second boundary information are grayscale images.

7. The particle detecting device as set forth in claim 5, wherein:
the measured value for the intensity of the third light is converted into a gradation value in the gradation scale.

8. The particle detecting device as set forth in claim 5, wherein:
the image of the first boundary information corresponds to an image wherein a three-dimensional coordinate system of the intensities of the first through third lights, including a multivariate function representing the discriminating boundaries, is observed from above the coordinate indicating the intensity of the third light; and
the image of the second boundary information corresponds to an image wherein a three-dimensional coordinate system, including a multivariate function, is observed from below the coordinate indicating the intensity of the third light.

9. The particle detecting device as set forth in claim 1, wherein:
the discriminating information corresponds to an image that is a slice, at an arbitrary value for the coordinate that indicates the intensity of the third light, in a three-dimensional coordinate system for the intensities of the first through third lights that includes the multivariate function that indicates the discriminating boundaries.

10. The particle detecting device as set forth in claim 1, wherein:
the discriminating information corresponds to an image that is a slice, at a maximum value, a minimum value, and an intermediate value for the intensity of the third light in the multivariate function, in a three-dimensional coordinate system for the intensities of the first through third lights that includes the multivariate function that indicates the discriminating boundaries.

11. A particle detecting method, comprising:
measuring measured values for intensities of first, second, and third lights of mutually differing wavelengths, produced by particles to be measured;
storing first boundary information wherein intensities of a third light at a discriminating boundary for a particle of a first classification and a particle of a second classification is recorded in a first range in a two-dimensional table of first and second light intensities;
preparing second boundary information wherein intensity of a third light at the discriminating boundary is recorded in a second range in the two-dimensional table;
preparing discriminating information wherein an identifier for a particle of the first classification is recorded in a cell that is bounded by the discriminating boundaries of the two-dimensional table and an identifier for a particle of the second classification is recorded in a cell that is not bounded by the discriminating boundaries;
acquiring identifiers for particles of the first and second classifications, from the discriminating information, and acquiring first and second boundary values for the intensity of the third light at the discriminating boundary, based on measured values for the intensities of the first and second lights; and
evaluating that the particle being measured is a particle of the first classification when the identifier for the particle of the first classification is acquired and the measured value for the intensity of the third light is between the first and second boundary values, and evaluating the particle being measured as being a particle of the second classification either when the identifier for a particle of the first classification is acquired and the measured value for the intensity of the third light is not between the first and second boundary values or when an identifier for a particle of the second classification is acquired.

12. The particle detecting method as set forth in claim 11, wherein:
the first and second lights are lights in the fluorescent band; and
the third light is scattered light.

13. The particle detecting method as set forth in claim 11, wherein:
the particle of the first classification is a biologic particle; and
the particle of the second classification is a non-biologic particle.

14. The particle detecting method as set forth in claim 11, wherein:
the particle of the first classification is a non-biologic particle; and
the particle of the second classification is a biologic particle.

15. The particle detecting method as set forth in claim 11, wherein:
the first and second boundary information are images wherein the intensities of the third light are represented as gradations.

16. The particle detecting method as set forth in claim 15, wherein:
the first and second boundary information are grayscale images.

17. The particle detecting method as set forth in claim 15, wherein:
the measured value for the intensity of the third light is converted into a gradation value in the gradation scale.

18. The particle detecting method as set forth in claim 15, wherein:
the image of the first boundary information corresponds to an image wherein a three-dimensional coordinate system of the intensities of the first through third lights, including a multivariate function representing the discriminating boundaries, is observed from above the coordinate indicating the intensity of the third light; and
the image of the second boundary information corresponds to an image wherein a three-dimensional coordinate system, including a multivariate function, is observed from below the coordinate indicating the intensity of the third light.

19. The particle detecting method as set forth in claim 11, wherein:
the discriminating information corresponds to an image that is a slice, at an arbitrary value for the coordinate that indicates the intensity of the third light, in a three-dimensional coordinate system for the intensities of the first through third lights that includes the multivariate function that indicates the discriminating boundaries.

20. The particle detecting method as set forth in claim 11, wherein:
the discriminating information corresponds to an image that is a slice, at a maximum value, a minimum value, and an intermediate value for the intensity of the third light in the multivariate function, in a three-dimensional coordinate system for the intensities of the first through third lights that includes the multivariate function that indicates the discriminating boundaries.

* * * * *